US006328724B1

(12) United States Patent
Ronnberg et al.

(10) Patent No.: US 6,328,724 B1
(45) Date of Patent: Dec. 11, 2001

(54) ABSORBENT ARTICLE, SUCH AS A DIAPER OR AN INCONTINENCE GUARD

(75) Inventors: Peter Ronnberg; Eva Fransson, both of Molndal; Anders Gustafsson, Billdal, all of (SE)

(73) Assignee: SCA Molnlycke AB, Gothenburg (SE)

( * ) Notice: Subject to any disclaimer, the term of this patent is extended or adjusted under 35 U.S.C. 154(b) by 0 days.

(21) Appl. No.: 09/380,307

(22) PCT Filed: Feb. 11, 1998

(86) PCT No.: PCT/SE98/00233

§ 371 Date: Feb. 4, 2000

§ 102(e) Date: Feb. 4, 2000

(87) PCT Pub. No.: WO98/37839

PCT Pub. Date: Sep. 3, 1998

(30) Foreign Application Priority Data

Feb. 28, 1997 (SE) .................................................. 9700730

(51) Int. Cl.[7] .................................................. A61F 13/15

(52) U.S. Cl. ................................ 604/385.24; 604/385.01; 604/385.19; 604/385.201; 604/385.24; 604/385.27; 604/385.28

(58) Field of Search ......................... 604/385.01, 385.19, 604/385.201, 385.24, 385.27, 385.28

(56) References Cited

U.S. PATENT DOCUMENTS 4,795,452 * 1/1989 Blaney et al. .................... 604/383.1
5,672,166 * 9/1997 Vandemoortele ................. 604/385.2
5,792,130 * 8/1998 Widlund et al. .................. 604/385.1
6,222,092 * 4/2001 Hansen et al. ....................... 604/378
6,254,583 * 7/2001 Coates ............................ 604/385.15

* cited by examiner

*Primary Examiner*—Aaron J. Lewis
*Assistant Examiner*—M. Bogart
(74) *Attorney, Agent, or Firm*—Young & Thompson

(57) ABSTRACT

An absorbent article includes a front part, a rear part and an intermediate crotch part and also an absorbent body enclosed between the outer liquid-impermeable casing sheet and an inner liquid-permeable casing sheet, and longitudinal flaps located on respective sides of the longitudinal symmetry axis of the article and that extend transversely in towards the axis, and further including longitudinal elastic elements which extend along those edges of the flaps that face toward the longitudinal symmetry axis. The absorbent body is divided into a central part and two side parts at least in the crotch part by folding indications which are located on respective sides of the longitudinal symmetry axis in front and rear sections and which diverge relative to one another up to the side edges of the absorbent body. The side flaps are joined to the outer casing sheet along its longitudinal edges; and each of the side flaps extends from a point in the crotch part on the inside of the article inwardly toward the longitudinal symmetry axis (AA) while decreasing in distance from the axis towards the front part and the rear part respectively up to a point in respective front and rear parts.

11 Claims, 2 Drawing Sheets

17 18 9 III 13 6 3 19 16 12 11 III 5 10

ABSORBENT ARTICLE, SUCH AS A DIAPER OR AN INCONTINENCE GUARD

CROSS REFERENCE TO RELATED APPLICATION

This is the 35 USC 371 national stage of international application PCT/SE98/00233 filed on Feb. 11, 1998, which designated the United States of America.

FIELD OF THE INVENTION

The present invention relates to an absorbent article, such as a diaper or an incontinence guard, having a front-part, a rear-part and an intermediate crotch-part and including an absorbent body enclosed between an outer, liquid-impermeable casing sheet and an inner liquid-permeable casing sheet and longitudinally extending flaps located on respective sides of the longitudinal, symmetry axis of the article and extending transversely to said axis and comprising longitudinally extending elastic elements that extend along those edges of the flaps that face towards said longitudinal symmetry axis, wherein the absorbent body is divided into a central part and two side-parts by means of folding indications at least in the crotch part of said article, wherein said folding indications extend mutually divergently to the side-edges of the absorbent body on respective sides of the longitudinal symmetry axis of said article in front and rear sections thereof.

BACKGROUND OF THE INVENTION

An absorbent article of this kind is known from SE-C2-502 548. The purpose of the longitudinally extending side-flaps is to impede the lateral flow of urine along the inner casing sheet of the article, and to prevent the wearer's skin coming into contact with excretement. Because the absorbent body is curved by virtue of the contraction of the elastic threads that extend along the edges of the flaps, a collecting volume is formed between the inner casing sheet and the inner surfaces of the flaps.

SUMMARY OF THE INVENTION

The object of the present invention is to increase this collecting volume to reduce the risk of lateral leakage when a person wearing the absorbent article lies on his/her side, and to reduce the risk of the side-flaps blocking the entrance of said collecting volume.

These objects are achieved in accordance with the invention by means of an absorbent article of the aforedescribed kind that is characterized in that the side-flaps are joined to the outer casing sheet along its longitudinal edges, and in that each of the side-flaps extends from a point in the crotch-part on the inside of said article, inwardly towards the longitudinal symmetry axis of said article at a distance from the longitudinal symmetry axis which decreases successively in a direction towards the front-part and rear-part respectively, up to a point in said front and said rear parts. Because the flaps extend right up to the side-edges of the outer casing sheet, the collecting volume is considerably increased. This collecting volume will be largest within those regions to which liquid will run when the person wearing the article lies on his/her side. The fact that the flaps are narrowest in the crotch-part eliminates the risk of the flaps blocking said entrance, while, at the same time, ensuring a safer sealing function by reason of the fact that the flap elastic can be positioned in the groins of the wearer.

In one preferred embodiment, the width of the flaps in their narrowest part will be smaller than 2 cm, while the width of the main-part of the absorbent body in its narrowest section located in the crotch-part will be at most 60% of the total width of the article in this section thereof, wherein the width of the flaps in their respective narrowest parts is smaller than half the width of the main-part of the absorbent body in its narrowest section located in the crotch-part. The article will also preferably include longitudinal elastic elements which extend along the side-edges of the article, at least in the crotch-part, on respective sides of the longitudinal symmetry axis of the article, so as to form so-called leg elastic, wherein when the article is held flat with the elastic elements stretched, the transverse distance between the outer limitation of the elastic elements that form said leg elastic and the inner limitation of the longitudinal elastic elements along the edges of the side-flaps in the narrowest part of said flaps is smaller than 3.5 cm. The longitudinal flaps in front and rear sections of the front and rear parts of the article extend longitudinally up to the longitudinal symmetry axis of the article and are joined together in these sections. The inner and the outer casing sheets extend beyond the absorbent body around the whole of its perimeter and are joined together at said parts which lie outside the absorbent body. When the article is held flat with the elastic elements stretched, the side-flaps will extend beyond the side-edges of the outer casing sheet and will include the longitudinally extending elastic elements that form leg elastic, and fastener devices which enable the side-edges of said article in said front and rear parts to be fastened together and therewith impart a pants-like configuration to said article. The side-flaps also extend longitudinally along the full length of the article. The folding indications will preferably have a width of at least $\sqrt{2}$ times the thickness of the absorbent body.

BRIEF DESCRIPTION OF THE DRAWINGS

The invention will now be described with reference to the accompanying drawings, in which.

DETAILED DESCRIPTION OF THE INVENTION

Figure 1:
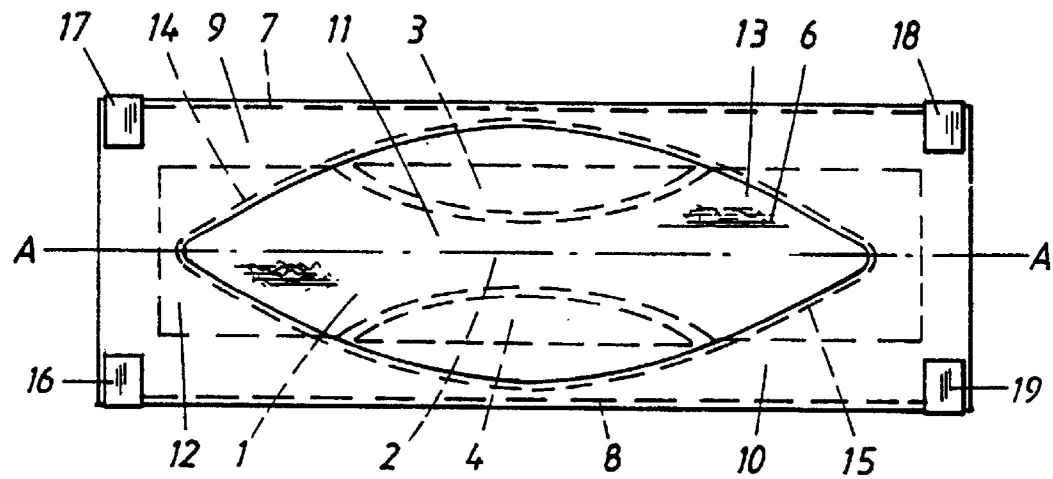
FIG. 1 illustrates a first embodiment of an inventive absorbent article from above.
Figure 2:
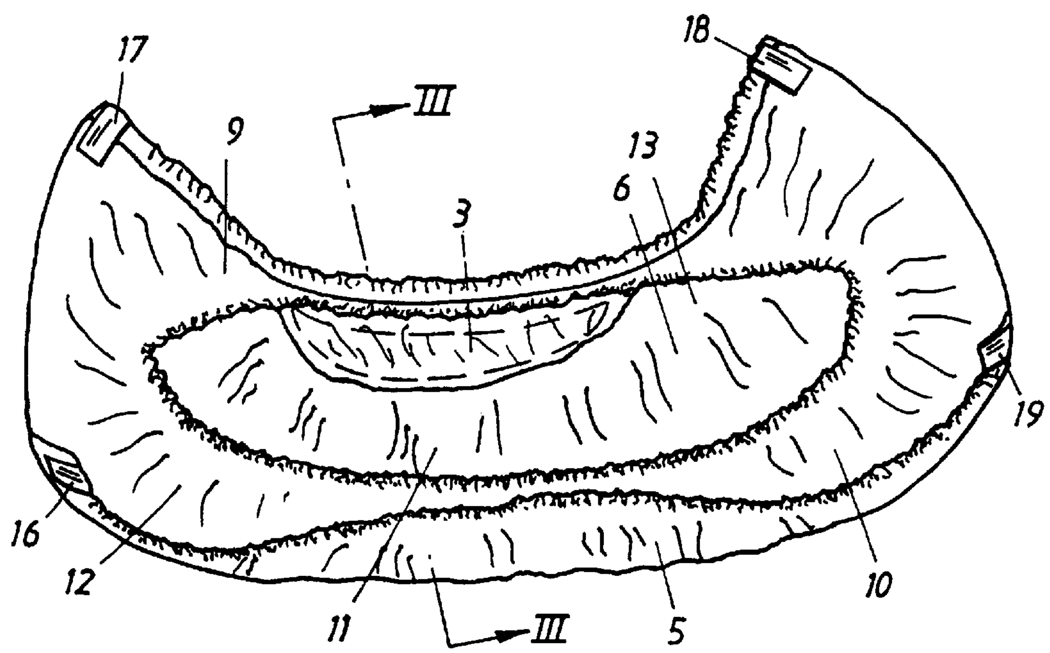
FIG. 2 is a perspective view of the article shown in FIG. 1.
Figure 3:
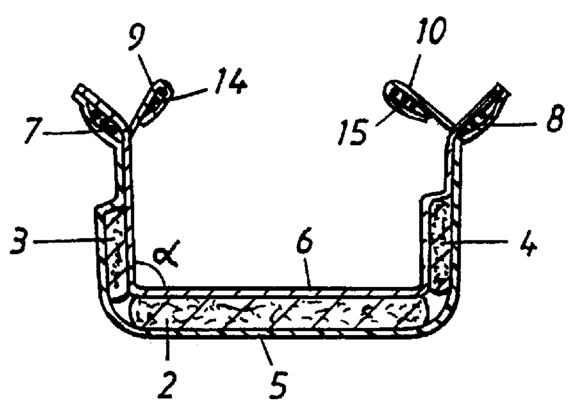
FIG. 3 is a sectional view taken on the line III—III in FIG. 2.

FIGS. 1–3 illustrate a first embodiment of an inventive diaper or incontinence guard. FIG. 1 shows the diaper in a flat state, i.e. with the elastic elements stretched, said diaper being held in this state during manufacture and prior to being packeted. FIGS. 2 and 3 show the diaper in a relaxed state, i.e. in the state assumed by the diaper when removed from its packet and before being placed on a diaper carrier.

The illustrated diaper includes an absorbent body 1 which is divided into a main-part 2 and two side-parts 3, 4, which are separated from the main-part by folding indications. The folding indications have a curved shape, such that the main-part 2 will obtain an hourglass configuration. The absorbent body 1 is comprised of air-laid cellulose fluff, although it may, of course, be made of any absorbent material that is used in the manufacture of absorbent bodies in diapers or incontinence guards. The absorbent body may be comprised of one or more layers and may or may not include so-called superabsorbents.

The absorbent body 1 is enclosed conventionally between an outer casing sheet 5 of liquid-impermeable material, such as polyethylene plastic, and an inner, liquid-permeable casing sheet 6, which is preferably comprised of nonwoven fabric. The outer and inner casing sheets may, of course, be comprised of material other than polyethylene and nonwoven fabric respectively. The casing sheets 5, 6 extend beyond the absorbent body 1 around the whole of its perimeter and are joined together at those parts which lie outside said absorbent body.

In the illustrated embodiment, the folding indications between the side-parts 3, 4 and the main-part 2 of the absorbent body 1 are obtained by separating the parts 3, 4 from the main-part 2 and separate therefrom by means of a gap in which the casing sheets 5, 6 are joined together. Naturally, these folding indications may be provided in other ways, e.g. by forming compression strings.

Elastic elements 7, 8 extend along respective longitudinal edges of the diaper. As will be evident from FIG. 3, the elastic elements 7, 8 of the illustrated embodiment are comprised of three prestretched or tensioned elastic threads mounted between the casing sheets 5, 6 and fastened thereto. Naturally, elastic ribbons or like devices can be used instead of threads, and the number of elements in the diaper may vary.

The diaper also includes flexible flaps 9, 10 that extend along the longitudinal edges of the diaper. These flaps are joined to the casing sheets 5, 6 along the longitudinal edges of the diaper and extend in over the inner casing sheet 6. The flaps 9, 10 are narrowest in the crotch-part 11 and extend from a point in said crotch-part towards respective front-part 12 and rear-part 13 while increasing successively in width in towards the longitudinal symmetry axis A—A of the diaper. In the illustrated embodiment, the flaps 9, 10 reach the longitudinal symmetry axis A—A at points slightly inwardly of the front and rear parts respectively, and extend from these points at a constant width up to the front-end and rear-end of the diaper respectively. The flaps are joined together at these areas of constant width and thereby form a hole-embodying top sheet. Elastic threads or elastic tapes 14, 15 are fastened to the flaps 9, 10 along the curved sections of their inner longitudinal edges.

The diaper also includes conventional fastener devices 16–19 for fastening together the side-edges of the front and the rear diaper parts, so as to obtain a diaper of pants-like configuration or for fastening the side-edges with the aid of a waist belt or like device. The fastener devices may be adhesive or mechanical. In the illustrated embodiment, the fastener devices are intended to coact with a waist belt and are fastened to the outer casing sheet and folded-in over the flaps 9, 10.

All of the elastic devices 7, 8, 14 and 15 are mounted in a stretched or tensioned state. These devices will thus strive to contract from their stretched state to a relaxed state. In the relaxed or non-loaded state of the diaper, arises when a diaper is removed from its packet, the elastic devices 7, 8, 14, 15 will contract and therewith pucker the flexible sheets 5, 6, 9, 10 to which they are fastened. As the flaps 9, 10 contract, the main-part 2 of the absorbent body 1 will curve and the side-parts 3, 4 of the absorbent body and the parts of the casing sheets 5, 6 that lie outside the main-part 2 of said absorbent body will fold upwards, i.e. so that those parts of the inner casing sheet that cover the inner surface of the side-parts 3, 4 will face towards each other. The stiffness or rigidity of the absorbent body 1 is such that the spring force exerted by the elastic devices will essentially only deform the body 1 by bending. This can readily be achieved by appropriate compression of a cellulose fluff body or with the aid of a multi-layer body whose bottom layer is comprised of a stiffer material, which may or may not be an absorbent material.

FIGS. 2 and 3 show the diaper of FIG. 1 in a relaxed state. As will be evident from these Figures, contraction of the flaps 9, 10 and associated bending or curving of the main-part 2 of the absorbent body 1 will cause the top sheet formed by said flaps to extend above and at a distance from the absorbent body 1. When the diaper is applied, the diaper is stretched slightly from the state shown in FIGS. 2 and 3, therewith increasing the spring force in the elastic elements. When the diaper has been applied, the elastic elements will therewith press the curved edges of the flaps 9, 10 resiliently against the wearer's body and the longitudinal edges of the diaper against the wearer's thighs. The major part of the curvature of the main-part 2 of said body will, however, remain after having placed the diaper on the wearer, and the main-part of said diaper will be spaced from the wearer's body, in addition to said ends.

FIG. 3 is a cross-sectional view of the diaper shown in FIG. 1, and illustrates the narrowest section of the main-part 2 in the crotch-part of said diaper. The main-part 2 is located furthest from the flaps 9, 10 in this section. In order to enable the side-parts 3, 4 to be folded-up perpendicular to the plane of the main-part without deforming said main-part or said side-parts, the folding indications will have a width which is equal to or greater than √2 times the thickness of the absorbent body 1. This configuration will be maintained when putting on the diaper, provided that the width of the crotch of the diaper carrier coincides with the width of said main-part 2. The main-part 2 is dimensioned for a mean crotch-width value in the category of user for which the diaper is intended. The crotch width of small children will normally lie between 3 to 4 cm, and in the case of adults between 4 to 7 cm. The angle a between the main-part 2 of the absorbent body and the side-parts 3, 4 of an applied diaper will therefore deviate to a relatively small extent from a right angle in the case of a standing wearer. Larger angular deviations may occur, however, as the wearer moves his/her legs. In order to ensure that discharged liquid will always be able to enter the space between the main-part 2 and the flaps 9, 10 unobstructed by the flaps, the width of the flaps must not be excessive in said crotch-part. The flaps will preferably not have a greater width than 2 cm at the place of the narrowest section of the main-part 2 of said absorbent body 1 in the crotch-part.

It has been found that the width of the main-part of the absorbent body in its narrowest section located in the crotch-part should be at most 60% of the total width of the diaper or absorbent article in this section, so as to achieve suitable bending or curving of the main-part and therewith hold the main-part distanced from the wearer's body over a major part of the length of said main-part of the absorbent body.

In addition to holding the main-part 2 of the absorbent body 1 distanced from the wearer's body, the elastic elements 14, 15 in the flaps 9, 10 are intended to press the flaps sealingly against the wearer's body and therewith prevent urine or excretement from coming into contact with that side of the flaps which lies against the wearer's body. It has been observed that an effective sealing function is achieved when the elastic elements of the flaps in the crotch-region are located in the wearer's groins. Such positioning prevents sideways movement of the flaps in the crotch-region, irrespective of the external forces to which the diaper may be subjected as the wearer moves. The leg elastic 7, 8 shall also be located in the vicinity of the wearer's groins in order to achieve an optimal sealing function. In order to enable such application of the elastic element 7, 8, 14, 15, the smallest distance between the outer limitations of the leg elastic 7, 8 and the inner limitations of adjacent flap elastic 14 and 15 respectively shall not exceed 3.5 cm when the diaper is held flat. This positioning of the leg and flap elastic respectively will thus provide a double sealing function against sideways leakage at the narrowest section of the diaper.

When large quantities of liquid are discharged simultaneously, as is often the case with adult wearers, the absorbent body is unable to absorb all of this liquid at once, and some of the liquid will therefore run along the inner casing sheet towards the lowest part of the diaper. Consequently, when a diaper wearer lies on his/her side, there is a risk of liquid collecting at the long edge of the front or the rear part of the diaper. When the flaps are narrow at these parts of the diaper, there is a risk of liquid running over the edges of the flaps and out over said flaps. In order to greatly reduce this risk, the flaps 9, 10 have their greatest width in these parts.

Figure 4:
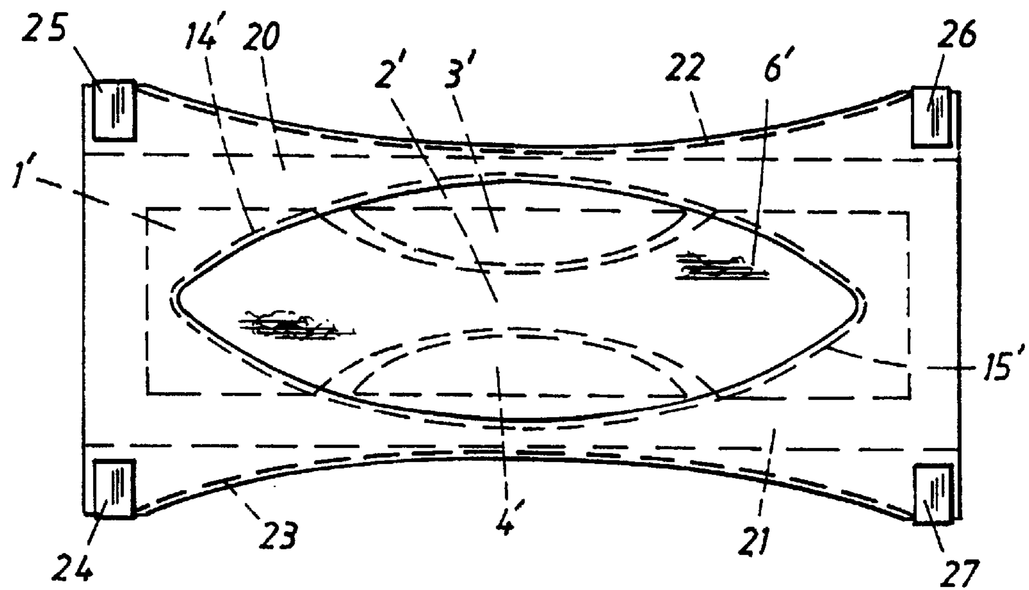
FIG. 4 is a view similar to the view of FIG. 1 and illustrates a second embodiment of an inventive article.

FIG. 4 shows a second embodiment of an inventive diaper. The sole differences of the diaper shown in FIG. 4 and that shown in FIGS. 1–3 is that the flaps 20, 21 of the FIG. 4 embodiment have parts that extend beyond the longitudinal edges of the casing sheets, that the leg elastic 22, 23 extends in these parts, and that the fastener devices 24–27 are fastened in said parts. The diaper is constructed in the same way as the aforedescribed diaper in other respects, and those components of the FIG. 4 embodiment that find correspondence in the embodiment shown in FIGS. 1–3 have been designated in FIG. 4 the same reference signs to which a prime has been added. This embodiment is beneficial from the aspect of manufacture, since all elastic is disposed on one single sheet that can be applied to the remainder of the diaper in a final stage of manufacture.

The flaps are made of a skin-friendly material, which may or may not be liquid-permeable. The flaps will preferably be comprised of an air-permeable material. An SMS material, i.e. a three-ply nonwoven material that includes a sheet of meltblown-nonwoven between two sheets of spunbond-nonwoven is an example of suitable material in this respect. Hydrophobic spunbond-nonwoven material is another example of material that can conceivably be used as flap material.

It will be understood that the described embodiments can be modified within the scope of the invention. For instance, the broadest parts of the flaps may have a width smaller than half the width of the diaper, or may have an other arcuate shape so as not to reach the longitudinal symmetry axis but to terminate in the end-edges of the diaper. Furthermore, the absorbent body may have a shape different to the illustrated rectangular shape in a flat state. It is also conceivable to manufacture the side-parts of the absorbent body from a material different to the main-part, and the side-parts need not necessarily be absorbent, even though this is preferred. Because of the deficient sealing function of the flaps, it is possible to omit leg elastic from the diaper, particularly when the flaps are made of liquid-impermeable material and form a top sheet as in the described embodiments. The inventive article may also conceivably coact with a pair of elastic pants instead of with a waist belt. The invention is therefore restricted solely by the scope of the following claims.

What is claimed is:

1. An absorbent article selected from the group consisting of a diaper and an incontinence guard, the article having a longitudinal symmetry axis and comprising:

a front part, a rear part, and an intermediate crotch part;

an absorbent body enclosed between an outer liquid-impermeable casing sheet having longitudinal edges and an inner liquid-permeable casing sheet;

longitudinal side flaps located on respective sides of the longitudinal symmetry axis and extending transversely in towards said axis;

longitudinal elastic elements extending along inner edges of the side flaps that face towards the longitudinal symmetry axis;

said absorbent body having side edges and being divided into a central part and two side parts at least in said crotch part by folding indications which are located on respective sides of the longitudinal symmetry axis in front and rear sections and which diverge relative to one another up to the side edges of the absorbent body;

said side flaps being joined to the outer casing sheet along its longitudinal edges;

each of the side flaps extending from a point in the crotch part inside of the article inwardly towards the longitudinal symmetry axis while decreasing in distance from said axis towards the front part and the rear part respectively up to a point in respective front and rear parts; and said side flaps being planar and without folds when the elastic elements are stretched and the article is held in a stretched state.

2. The absorbent article according to claim 1, wherein the side flaps have a narrowest part which has a width of less than 2 cm.

3. The absorbent article according to claim 2, wherein the central part of said absorbent body has a narrowest section located in said crotch part; said narrowest section having a width which corresponds to at most 60% of a total width of the article in said section.

4. The absorbent article according to claim 3, wherein the width of the side flaps in their narrowest parts is smaller than half the width of the narrowest section of said central part of the absorbent body located in said crotch part.

5. The absorbent article according to claim 2, further comprising longitudinal elastic devices which extend along side edges of said article, at least in the crotch part thereof, on respective sides of the longitudinal symmetry axis so as to form leg elastic, when the article is held flat with the elastic elements and elastic devices stretched, the transversal distance between an outer limitation of the elastic devices and an inner limitation of adjacent elastic elements extending longitudinally along the edges of the side flaps in the narrowest part of the flaps is smaller than 3.5 cm.

6. The absorbent article according to claim 1, wherein the longitudinally extending side flaps in front and rear sections of the front and rear parts of the article extend right up to the longitudinal symmetry axis and are mutually joined in these sections.

7. The absorbent article according to claim 1, wherein the inner and outer casing sheets extend beyond the absorbent body around the whole of its perimeter and are mutually joined at parts which lie outside the absorbent body.

8. The absorbent article according to claim 1, wherein when the article is held flat with the elastic elements stretched, the side flaps extend beyond the longitudinal edges of the outer casing sheet and include longitudinal elastic devices forming leg elastic, said article further comprising fastener devices that enable side edges of the article in said front and rear part to be joined together to obtain an article of pants-shaped configuration.

9. The absorbent article according to claim 1, wherein the side flaps extend along a full length of the article in a longitudinal direction.

10. The absorbent article according to claim 1, wherein the folding indications have a width that corresponds at least to the square root of 2 times the thickness of the absorbent body in cm.

11. An absorbent article selected from the group consisting of a diaper and an incontinence guard, the article having a longitudinal symmetry axis and comprising:

a front part, a rear part, and an intermediate crotch part;

an absorbent body enclosed between an outer liquid-impermeable casing sheet having longitudinal edges and an inner liquid-permeable casing sheet;

longitudinal side flaps located on respective sides of the longitudinal symmetry axis and extending transversely in towards said axis;

longitudinal elastic elements extending along inner edges of the side flaps that face towards the longitudinal symmetry axis;

said absorbent body having side edges and being divided into a central part and two side parts at least in said crotch part by folding indications which are located on respective sides of the longitudinal symmetry axis in front and rear sections and which diverge relative to one another up to the side edges of the absorbent body;

said side flaps being joined to the outer casing sheet along its longitudinal edges;

each of the side flaps extending from a point in the crotch part inside of the article inwardly towards the longitudinal symmetry axis while decreasing in distance from said axis towards the front part and the rear part respectively up to a point in respective front and rear parts; and wherein the side flaps have a narrowest part which has a width of less than 2 cm.

* * * * *